(12) United States Patent  
Kannengiesser et al.

(10) Patent No.: US 8,598,873 B2  
(45) Date of Patent: Dec. 3, 2013

(54) MAGNETIC RESONANCE METHOD AND APPARATUS FOR TIME-RESOLVED ACQUISITION OF MAGNETIC RESONANCE DATA

(75) Inventors: Stephan Kannengiesser, Wuppertal (DE); Peter Schmitt, Weisendorf (DE); Michael Zenge, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 904 days.

(21) Appl. No.: 12/700,191

(22) Filed: Feb. 4, 2010

(65) Prior Publication Data

US 2010/0194390 A1    Aug. 5, 2010

(30) Foreign Application Priority Data

Feb. 4, 2009   (DE) .................. 10 2009 007 361

(51) Int. Cl.  
*A61B 5/055* (2006.01)  
*G01R 33/563* (2006.01)  
*G01R 33/561* (2006.01)

(52) U.S. Cl.  
USPC ........................... 324/309; 324/307; 600/410

(58) Field of Classification Search  
USPC .......................... 324/300–322; 600/407–435; 382/128–131  
See application file for complete search history.

(56) References Cited

U.S. PATENT DOCUMENTS

| | | | |
|---|---|---|---|
| 6,400,151 B1 * | 6/2002 | Haase et al. ................. | 324/309 |
| 6,577,127 B2 | 6/2003 | Harvey et al. ................ | 324/307 |
| 7,535,226 B2 * | 5/2009 | Takahashi et al. ........... | 324/309 |
| 7,659,720 B2 * | 2/2010 | Furudate et al. ............. | 324/318 |
| 7,821,267 B2 * | 10/2010 | Yatsui et al. .................. | 324/318 |
| 7,834,624 B2 * | 11/2010 | Arnold ......................... | 324/307 |
| 8,008,918 B2 * | 8/2011 | Sugiura ........................ | 324/318 |
| 2003/0004408 A1 | 1/2003 | Zhu .............................. | 600/410 |
| 2005/0054910 A1 * | 3/2005 | Tremblay et al. ............ | 600/411 |
| 2006/0262340 A1 | 11/2006 | Lee .............................. | 358/1.14 |
| 2008/0111546 A1 * | 5/2008 | Takahashi et al. ............ | 324/307 |
| 2008/0116892 A1 | 5/2008 | Laub et al. ................... | 324/312 |
| 2008/0180104 A1 * | 7/2008 | Furudate ...................... | 324/318 |
| 2008/0218166 A1 * | 9/2008 | Arnold ......................... | 324/307 |
| 2009/0309595 A1 * | 12/2009 | Yatsui .......................... | 324/309 |
| 2010/0052676 A1 * | 3/2010 | Sugiura ........................ | 324/309 |
| 2010/0201360 A1 * | 8/2010 | Morita ......................... | 324/309 |

OTHER PUBLICATIONS

"Continuously Moving Table Data Acquisition Method for Long FOV Contrast-Enhaneed MRA and Whole-Body MRI," Kruger et al., Magnetic Resonance in Medicine vol. 47, (2002) pp. 224-231.  
"Time-Resolved 3D Contrast-Enhanced MRA of an Extended FOV Using Continuous Table Motion," Madhuranthakam et al., Magnetic Resonance in Medicine vol. 51, (2004) pp. 568-576.  
"Interactive Continuously Moving Table (iCMT) Large Field-of-View Real-Time MRI," Sabati et al., Magnetic Resonance in Medicine vol. 55, (2006) pp. 1202-1209.

* cited by examiner

*Primary Examiner* — Melissa Koval  
*Assistant Examiner* — Tiffany Fetzner  
(74) *Attorney, Agent, or Firm* — Schiff Hardin LLP

(57) ABSTRACT

In a method and apparatus for time-resolved acquisition of magnetic resonance (MR) data, an examination subject is continuously moved through the examination region of an MR scanner, and MR signals are acquired. Prior to the acquisition of MR signals, a phase coding that corresponds to a position for data entry in k-space is carried out. An interruption of the movement of the subject takes place at a predetermined table position, and the acquisition of MR signals is continued over the course of a predetermined time period, while the subject is at rest in the predetermined position. At least while the subject is at rest, the phase coding causes acquisition of a predetermined number of MR signals for filling a first region of k-space to alternate with MR data and a predetermined number of MR signals for filling a second region of k-space.

23 Claims, 4 Drawing Sheets

MAGNETIC RESONANCE METHOD AND APPARATUS FOR TIME-RESOLVED ACQUISITION OF MAGNETIC RESONANCE DATA

BACKGROUND OF THE INVENTION

1. Field of the Invention

The present invention concerns a process for acquiring time-resolved magnetic resonance data as well as a magnetic resonance imaging scanner for that purpose. In particular, the process can be used for contrast enhanced magnetic resonance angiography (CE-MRA).

2. Description of the Prior Art

Magnetic resonance imaging is a frequently used imaging process that is used for medical problems in particular. With the conventional magnetic resonance imaging (MRI), a person or an object that is to be examined is placed in an examination region of the magnetic resonance imaging scanner. A static basic magnetic field ($B_0$), which is as homogenous as possible, is generated in the region to be examined, through which the nuclear spin of the object being examined are aligned with the basic magnetic field. Through irradiation of the object being examined with radio frequency (RF) pulses, the nuclear spins are deflected from this alignment. During a relaxation of the nuclear spin, a radio frequency signal is emitted, which is then detected as a magnetic resonance signal. In this manner, by applying a number of magnetic field gradients, a spatial coding can be obtained. From the acquired magnetic resonance data, an image can be reconstructed, which shows internal details of the object being examined.

In order to obtain a sufficient image quality, it is necessary with conventional methods to acquire the magnetic resonance data with the object being examined in a state of rest over the course of a certain period of time. Enlargement of the area being examined, wherein the basic magnetic field exhibits a sufficient homogeneity, is, however, subject to limitations. With more recent magnetic resonance imaging processes, in order to scan a larger area the scanning table on which the object being examined is placed is moved constantly through the examination region. During this so-called "continuous table movement" (CTM), magnetic resonance data are recorded and reconstructed. In this manner, a seamless image of a large region of the object being examined can be generated from a single scan.

One example of this application is the contrast enhanced magnetic resonance angiography (CE-MRA), wherein a contrast agent is introduced into the object being examined, and whereby the contrast agent bolus subsequently circulates through the circulatory system. Through the movement of the table, the scanning of the magnetic resonance data can follow the contrast agent bolus through the body of the object being examined. An examination of this type may use rapid gradient systems, an automatic table movement as well as TIM (total imaging matrix) technology. In this manner, the contrast agent bolus can be followed from the renal arteries to the soles of the feet with high image quality and without imaging of the venous phase. The TIM technique in combination with a continuous table movement (TIM-CT) allows for a seamless vascular imaging of the object being examined.

For images to diagnose certain diseases, such as a peripheral arterial obstructive disease, the contrast agent may be injected, for example, in both feet of a subject at different points in time. In order to reliably separate arteries from veins, particularly with imaging for a serious disease, a time-resolved acquiring of image data is necessary. As an example, image data from early, middle, and late phases of the contrast agent injection may be acquired in order to separate arteries from veins. For this purpose, it is preferable for the magnetic resonance data to be acquired at a frequency which is as high as possible. In order to improve the time-resolution, so-called "view sharing" methods may be used. A view sharing of this type during continuous table movement however, requires corrections for non-linearities in the magnetic field gradients, and thus is only compatible to a degree.

In particular, the TIM-CT process, which uses a reconstruction time-optimized correction for non-linearities in the magnetic field gradients, cannot be combined with view sharing. The use of a generalized solution for the gradient correction in order to avoid this problem is not practical, as this requires a very long period for reconstruction. Furthermore, it is frequently not necessary to perform a temporal resolution of proximal parts of recorded image data sets, as a considerable delay in the influence of the contrast agent can be regularly observed in the distal regions of the person being examined. When view sharing is combined with the magnetic resonance data obtained with a continuous table movement, a correlation between the temporal and spatial resolution occurs, i.e. in order to achieve a higher temporal resolution, a lower spatial resolution must be accepted.

As a result, there is a need for a for a method acquiring magnetic resonance data that provides both a high image quality as well as high temporal resolution, particularly in the distal regions of the object being examined. The process should make it possible to obtain an image with an improved temporal resolution of the distribution of the contrast agent in a magnetic resonance angiography examination. Furthermore, it is desirable to acquire the magnetic resonance data with a continuous table movement, in order that even with very short magnets, image data of an object being examined of any size may be obtained. It is also desirable for the process to be comprised of a limited number of steps and simple scanning procedures in order that an optimal work flow is obtained. The process should also achieve a reduction in time and costs in comparison with conventional methods.

SUMMARY OF THE INVENTION

An object of the present invention is to provide an improved method for acquiring time-resolved magnetic resonance data that achieves the above needs.

In accordance with a first aspect of the present invention, in a method for acquiring time-resolved magnetic resonance data from an examination region in a magnetic resonance imaging scanner, the object to be examined is placed on a table and continuously moved through the examination region, and magnetic resonance signals are acquired from the examination region while the object being examined is moved continuously by the table through the examination region. Prior to the acquisition of magnetic resonance signals, a phase coding, which corresponds to a position in a k-space for the sampling of the k-space, is implemented with interruption of the movement of the table at a predetermined position, followed by a continuation of the acquisition of magnetic resonance signals from the examination region over the course of the predetermined period, while the table is resting at the predetermined position. At least during the resting period of the table, the phase coding is implemented such that acquisitions are of a predetermined number of magnetic resonance signals for the purpose of filling a first region of the k-space with magnetic resonance data, that alternate with a predetermined number of magnetic resonance signals for filling the a second region of the k-space with magnetic resonance data.

With this method, it is possible to reconstruct a static, i.e. a non-time-resolved image data set which displays the object being examined from the magnetic resonance data recorded during the movement of the table. With a table which is at rest, it is subsequently possible to record a time-resolved series of magnetic resonance data sets, so it is also possible to obtain a high temporal resolution through the use of a view sharing process. With the table in a resting state it is possible in this manner, for example, to follow the movement of a contrast agent through the circulatory system of the object being examined. In this manner, both a high spatial, as well as temporal resolution may be obtained. Furthermore, with a method of this sort, it is possible to achieve an optimal work flow, as the steps of the process can be automatically carried out consecutively for the most part. The object being examined can, for the most part, be examined in a single passage, so the distal end, which is located in the examination region on the table at rest, can be displayed in a time-resolved manner. With the alternating acquisitions of magnetic resonance signals for two regions of the k-space, it is possible to obtain an efficient reconstruction of image data while also allowing a view sharing process to be carried out, which provides a high time-resolution. Naturally, it is also possible to execute an appropriate phase coding with a moving table, so that a view sharing process may be used to reconstruct image data from the recorded magnetic resonance data obtained thereby. This may require a lengthy computation period, however, because sampling of the k-space with a moving table of this type should incorporate a generalized gradient correction.

In accordance with one design version of the process of the invention, the phase coding takes place in two spatial directions, with the first regional points in k-space having a radial distance to a center of the k-space which is below a predetermined limit value, and the second regional points in the k-space having a radial distance to the center of the k-space which exceeds the predetermined limit value.

A subdivision of the k-space of this type allows for points in the center of the k-space, which primarily responsible for the contrast in reconstructed image data, to be sampled more frequently than points in the second, outer region. In this manner, a good image quality can be ensured for larger time-resolutions.

The first region of the k-space may be sampled, for example, with a single spiral trajectory, and the second region of the k-space may be sampled with at least two spiral trajectories. The first region can contain, for example, predetermined points to be sampled which for the most part may be sampled with the single spiral trajectory. The second region can contain, for example, predetermined points to be sampled, whereby a part of said predetermined points are sampled by one of the spiral trajectories. The second spiral trajectory can then sample the rest of the predetermined points in a subsequent scanning. Furthermore, it can be ensured that through the spiral trajectory, the magnetic resonance data from different regions of the k-space are recorded in the different acquiring steps.

K-space is ideally sampled at predetermined points within the first region and the second region, whereby the predetermined points are arranged such that they determine a sampling trajectory according to their radial distance to a center of k-space and an azimuth angle, which describes their position in k-space. An arrangement of this sort of the points to be sampled allows for an efficient computation of a spiral sampling trajectory, for example.

The sampling of the first region can take place in at least one sampling sequence wherein the radial distance of the points increases, and a sampling sequence wherein the radial distance of the points decreases, with each sampling sequence covering different predetermined points. In this manner the first region can be sampled, for example, with an expanding spiral trajectory that contains half of the points to be sampled, and a second contracting spiral trajectory that contains the other half of the points to be sampled. In this manner, also with a moving table, an efficient and for the most part artifact-free reconstruction of image data from the recorded magnetic resonance data can be ensured.

The sampling of the second region may contain at least one sampling sequence in which the radial distance of the points increases, and one sampling sequence in which the radial distance of the points decreases. Each sampling sequence may contain different predetermined points, so in one sampling of the second region, half or less of the predetermined points lying in the second region are sampled. The sampling sequence for the second region may be composed of, for example, one expanding spiral trajectory and one contracting spiral trajectory, with these trajectories, in each case, sampling only every fourth predetermined point, so that only half of the predetermined points are sampled in the sampling sequence. The rest of the predetermined points may be acquired in either a prior or subsequent sampling of the magnetic resonance data in the second region. In this manner, on the whole, it is possible to make a faster acquiring of the magnetic resonance data, and as a result, obtain a higher temporal resolution.

K-space may be sampled at predetermined points, whereby with each sampling of the second region, magnetic resonance data is recorded for only part of the predetermined points in the second region, and whereby magnetic resonance data for the other part of the predetermined points is recorded in a previous and/or subsequent sampling of the second region. An image reconstruction on the basis of the recorded magnetic resonance data can be obtained for the first region, whereby the image reconstruction makes use of the other magnetic resonance data which is recorded in at least one prior sampling and at least one subsequent sampling of the second region. In this manner, the duration of the entire magnetic resonance imaging scanning may be reduced and the time-resolution of the time series of magnetic resonance data may be increased.

In this version furthermore, a reconstruction may be obtained of a time series of image data from the layers of the first region and the second region of the recorded magnetic resonance data of the k-space. The time series can be reconstructed from the recorded magnetic resonance data of either an immobile table and/or a continually moving table.

Preferably, the phase coding for a moving table is carried out such that the k-space is sampled in a grid array at predetermined points. A sampling of this type may be executed, for example, either horizontally or vertically. In other words, it is not executed in the same manner as with an immobile table, whereby the k-space is divided into two regions, but rather all of the k-space points are sampled in a grid array consecutively. After magnetic resonance data for all of the predetermined points has been recorded, the sampling may be repeated. A sampling of this sort may be used particularly with an optimized computing time gradient correction, whereby the necessary computing time can be reduced for image reconstruction. Preferably, a static image data set is reconstructed thereby.

In accordance with another embodiment, the phase coding can be implemented in two spatial directions, with a frequency coding additionally being implemented in a third spatial direction that is substantially parallel to the movement direction of the table, and additionally a partial reconstruction of the acquired magnetic resonance data is carried out with a moving table, such that the magnetic resonance data in the direction of the frequency coding is transformed in the space and is arranged according to the position of the table in the direction of movement that it is recorded in. The acquired magnetic resonance data can, for example, be distributed in a so-called hybrid space, which is defined by the wave vectors $k_x$ and $k_y$, and in a third axis by the spatial vector z. In this manner, an effective processing of the acquired magnetic resonance data is made possible for a moving table, as well as the reconstruction of a nearly seamless image data set of the region to be imaged of the object under examination.

The subject being examined may have a contrast agent bolus in his or her circulatory system, whereby the velocity of the table corresponds for the most part to the velocity of the contrast agent bolus in the circulatory system of the object being examined. In this manner, the magnetic resonance data with a moving table will for the most part only be recorded from the arterial phase of the contrast agent distribution in the circulatory system of the object being examined. With this so-called "bolos chase" method, the arteries of the object being examined can be scanned within a region which is larger than the examination region of the magnetic resonance imaging scanner.

The examination region of the magnetic resonance imaging scanner, from which magnetic resonance data is recorded, may be of a predetermined length parallel to the direction of movement of the table, whereby the velocity of the table is configured such that the table is moved between a repeated sampling of the same predetermined point in the k-space and at least half of the predetermined length. In this manner, a limited spatial overlapping of the recorded magnetic resonance data may be obtained, whereby the acquiring process can be accelerated. Furthermore, an overlapping in this manner ensures a good quality reconstruction of image data.

Furthermore, this can provide for a correction of the recorded magnetic resonance data with a moving table, or, rather, of reconstructed image data, for non-linearity of magnetic field gradients. The correction is designed, for example, for a grid array sampling of k-space and can be executed online, while the table is moved through the examination region. In this manner it is possible to both carry out a rapid gradient correction as well as, with an immobile table, to record a time series with high resolution using a view sharing process. By using an optimized computation time gradient correction, which is carried out during the acquisition of the magnetic resonance data, the time required to reconstruct a relevant image data set can be significantly reduced. With a moving table, a correction of the magnetic resonance data of this sort can also be carried out by using a view sharing process.

The object being examined can be a person, whereby the predetermined position of the table is configured such that a distal end of the person being examined is located within the examination region. The distal end may be a foot, for example, of the person being examined. The object being examined may display a contrast agent in its circulatory system, whereby, with an immobile table, magnetic resonance data is recorded which allows for the reconstruction of a time series of image data, containing at least three phases of the contrast agent distribution in the circulatory system. In this manner, an early, middle and late phase of the contrast agent distribution, for example, in the feet, can be examined.

In accordance with another embodiment, a reconstruction of a static image data set is carried out of the magnetic resonance data acquired during the movement of the table, whereas the magnetic resonance data acquired from an immobile table are used to create a reconstruction of a time resolved image data set. In this manner, the magnetic resonance data for a moving table can be recorded more rapidly than is possible when a time series of image data is to be reconstructed for this region. The static image data set displays, for example, the region of the object being examined which would be moved through the examination region. A reconstruction of a time series of image data can thereby be obtained which is combined, for each time step of the time series of the static image data set, with an image data set for a time step of the captured time-resolved image data set for an immobile table, such as a distal end of the object being examined. In this manner, the image data for each time step contains the entire visual field examined, although only the distal region is actually time-resolved.

Furthermore, acquisition of magnetic resonance can be done signals with an immobile table before acquiring the magnetic resonance signals with a moving table. By acquiring a magnetic resonance data set with an immobile table for both the proximal as well as the distal end of the entire visual field, "partial Fourier" artifacts, i.e. artifacts that occur due to k-space being only partially filled, may be avoided. Furthermore, with an immobile table, the distal end of the entire visual field may be captured with greater spatial resolution, for example, than the rest of the visual field.

The present invention also encompasses a magnetic resonance imaging scanner for acquiring time-resolved magnetic resonance data in an examination region of the magnetic resonance imaging scanner. The magnetic resonance imaging scanner has a table, which is designed to transport an object to be examined continuously through the examination region, an acquisition unit for acquiring magnetic resonance signals from the examination region, a gradient unit for generating a magnetic field gradient in the examination region, and a control unit, which controls the table, the acquisition unit and the gradient unit. The control unit is configured for controlling the acquisition of magnetic resonance signals from the examination region, while the object being examined is transported continuously through the examination region, and prior to the acquisition of magnetic resonance signals, a phase coding, which corresponds to a position in the k-space, using the gradient unit to sample the k-space is carried out, with the phase coding causing alternating acquisitions to be made of a predetermined number of magnetic resonance signals for filling a first region of the k-space with magnetic resonance data, and a predetermined number of magnetic resonance signals for filling a second region of the k-space with magnetic resonance data. The movement of the table is interrupted at a predetermined position; and the acquisition of magnetic resonance signals in the examination region is continued over the course of a predetermined time period, while the table is at rest in the predetermined position.

The previously specified advantages may be similarly achieved with the magnetic resonance imaging scanner.

Furthermore, the invention encompasses computer-readable medium encoded with a computer program that, by installing in a computer system, will execute the previously specified processes. The control unit of a magnetic resonance imaging scanner can, for example, be such a computer system.

Naturally, the characteristics of the previously described design versions and aspects of the present invention may be combined.

DESCRIPTION OF THE PREFERRED EMBODIMENTS

Figure 1:
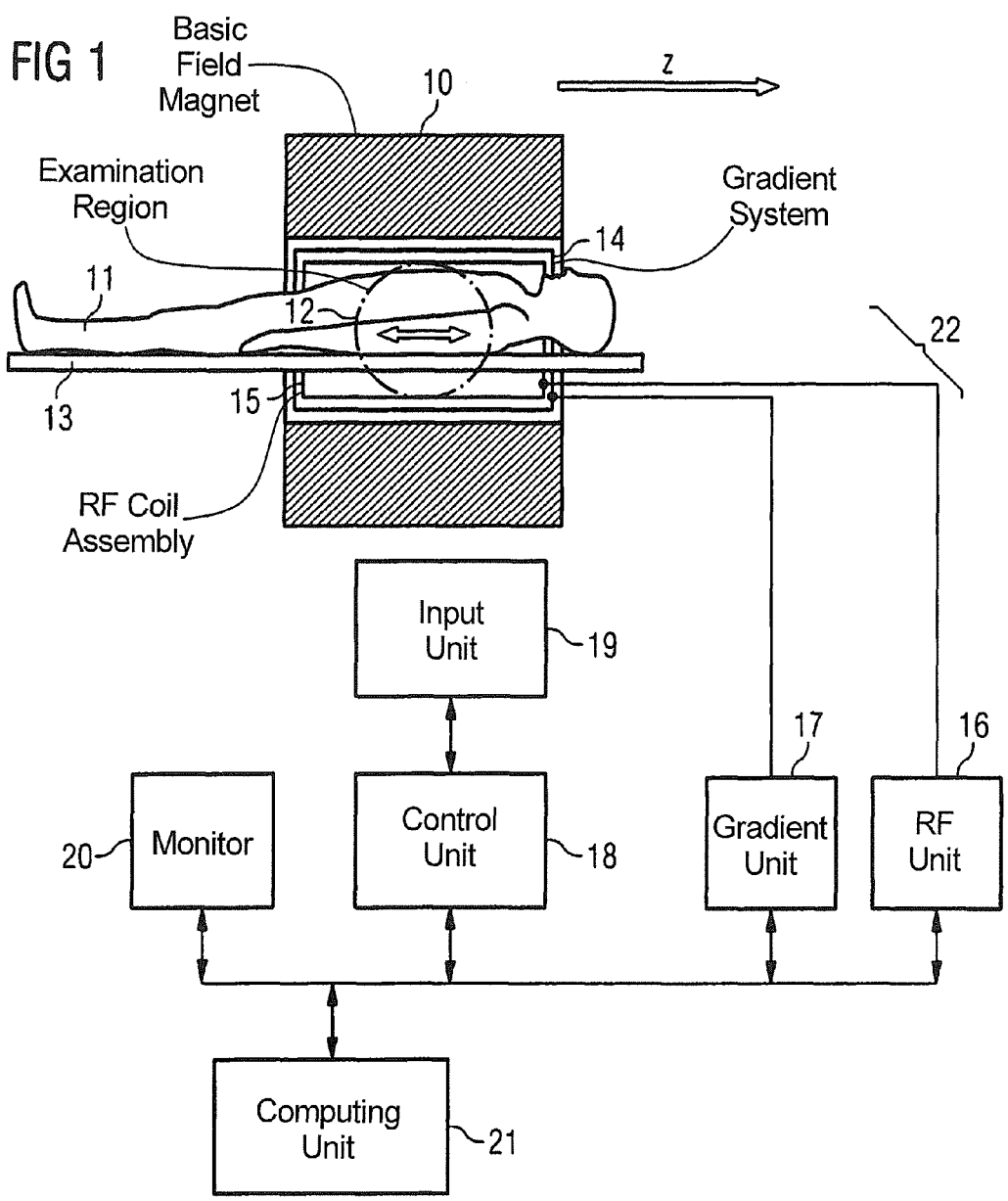
FIG. 1 is a schematic presentation of a magnetic resonance imaging scanner in accordance with an embodiment of the present invention.

FIG. 1 schematically shows a magnetic resonance imaging scanner, which is designed to acquire time-resolved magnetic resonance data. A magnetic resonance imaging (MRI) scanner of this sort contains a basic field magnet 10 for generating a polarization field $B_0$. An object being examined, in this case a person 11, may be transported on a table 13 into the magnet 10, as is schematically shown by the arrow. By moving or driving the table 13, the person 11 can be transported through the examination region 12 of the magnetic resonance imaging scanner, with magnetic resonance signals from the examination region 12 then being acquired. The magnet 10 may be designed to be significantly shorter in the lengthwise direction (z-axis), than is shown in FIG. 1.

The MRI scanner furthermore has a gradient system 14 for generating magnetic field gradients which are use for imaging and spatial coding. A spatial coding may be obtained through frequency coding in the lengthwise or z axis, whereas a phase coding can be generated in the x and y axis using the gradient system 14. In order to stimulate the polarization occurring in the main magnetic field, a radio frequency (RF) coil assembly 15 is used, which irradiates a radio frequency field in the person being examined 11, in order to deflect the magnetization from the equilibrium position.

In order to control the magnetic field gradients, a gradient unit 17 is used, and to control the radiated RF pulse, an RF unit 16 is used. The RF system may include an additional receiving coil, e.g. surface coils for receiving magnetic resonance signals as well as a unit for processing these signals. These elements, 14-17, may be characterized collectively as a receiving unit 22.

A control unit 18 centrally controls the magnetic resonance imaging scanner. The selection of the imaging sequence may be made through the control unit 18, for example. In this manner, an operator may select a sequencing protocol through the input unit 19, so reconstructed image data may be displayed on a display monitor 20. A reconstruction may be carried out, for example, by using the computing unit 21, e.g. with the appropriate algorithms.

The general operation of an MRI scanner is known to those of ordinary skill in the field, so a detailed description of the general components is not necessary.

The control unit 18 controls, for example, the transport of the table 13, as well as the radiation of RF pulses via the RF unit 16 and the generation of magnetic field gradients via the gradient unit 17. The magnetic resonance data, which correspond to the magnetic resonance signals recorded by a receiving coil, are also gathered by the control unit 18. These can be subsequently transmitted to the computing unit 21 in order to carry out a Fourier transformation. The control unit 18 is configured to be able to carry out the following process described in FIG. 2.

Figure 2:
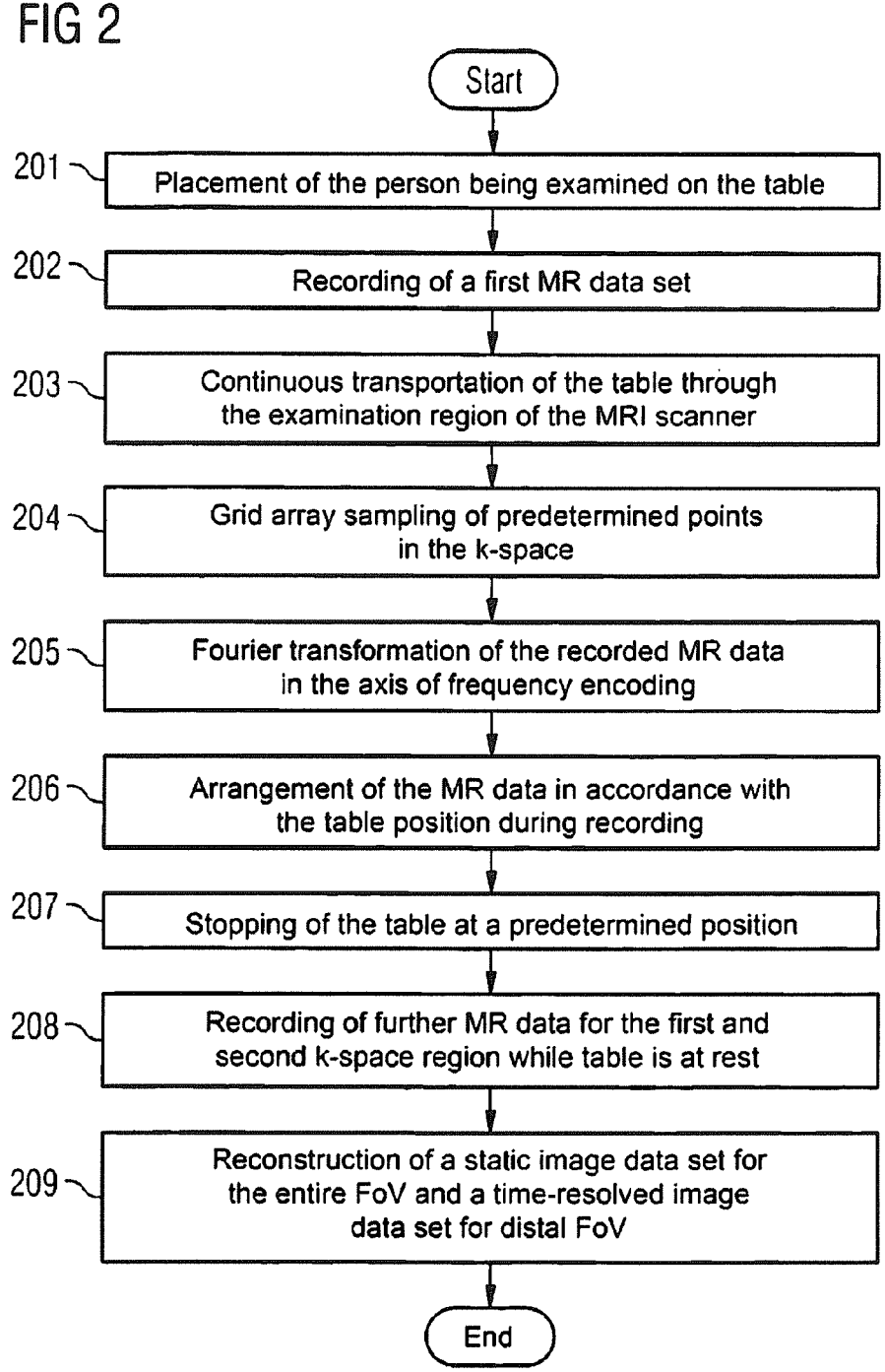
FIG. 2 is a flowchart that shows a process in accordance with an embodiment of the present invention.

FIG. 2 illustrates an embodiment of the process in accordance with the invention. In a first step 201, a person 11 to be examined is positioned on a table 13. The table 13 can then be transported to a starting position, and a contrast agent may be injected into the circulatory system of the person 11. This is followed by acquisition of a first MRI data set, for example, through a grid array sampling of the k-space, in step 202. A point in the k-space, that corresponds to a Fourier transformed space, is established, as is known, through a certain phase coding or frequency coding. In the present case, a frequency coding takes place in the longitudinal or z axis, i.e. parallel to the movement direction of the table, whereas a phase coding takes place in the x and y axis. In recording a magnetic resonance data set, the k-space is filled with data, whereby for various phase codings in the x and y axis, in each case a frequency encoded magnetic resonance signal is recorded. The recording of the first magnetic resonance data set takes place while the table is at rest, in order that "partial Fourier" contamination may be avoided.

Figure 3:
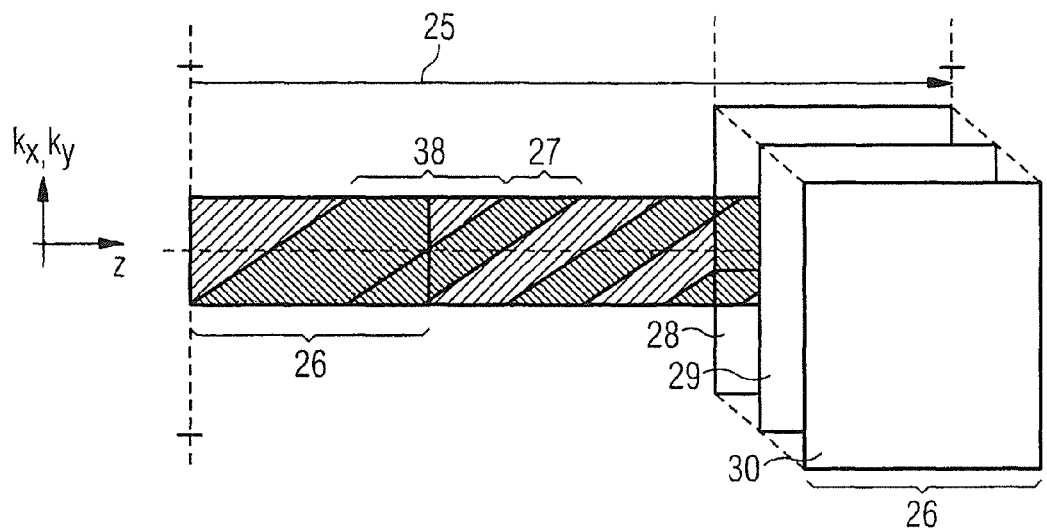
FIG. 3 schematically illustrates the acquisition of magnetic resonance data for various regions of an object being examined.

The situation is schematically shown in FIG. 3. FIG. 3 shows a so-called hybrid space, which is composed of spatial axes, in this case the z axis, and a k-space axis, either the $k_x$ or $k_y$ axis. The reference number 25 indicates the entire field of view (FoV) to be acquired. The reference number 26 indicates the longitudinal length of the examination region 12 in the magnetic resonance imaging scanner, i.e. the length corresponding to a frequency coding in the recording of a magnetic resonance data set. As is indicated in the figure, an MRI data set is recorded next in step 202, which creates an image of the area 26.

In step 203 the table is transported continuously through the examination region of the magnetic resonance imaging scanner. During the transportation of the table, a grid array sampling of predetermined points in k-space is carried out in step 204, whereby MRI data are acquired for the predetermined points. While the table is moving, frequency encoded magnetic resonance data for the various values of $k_x$ and $k_y$, which are determined according to the phase coding, are recorded. Because the recording process requires a certain amount of time, during which the table is moving, the recorded data corresponds to different z positions. This is indicated in FIG. 3 for a k-space dimension by the diagonal lines, whereby the area between said lines corresponds to a partial FoV. Because of this, in order to obtain a complete data set, the recorded magnetic resonance data in the frequency coding axis is Fourier transformed (step 205), and arranged according to the position of the table during the recording process (step 206). When all of the magnetic resonance data have been acquired for the predetermined points to be sampled in k-space, the phase coding sequence is repeated, and the relevant points are re-sampled. During this, the table is moved along a distance 38. As this is shorter than the illustrated distance 26 of the examination region, an overlapping occurs. This overlapping ensures that the magnetic resonance data of the field of view is complete.

In addition, a position correction may be carried out for the moving table. A sub-pixel position correction may be carried out by rotating the phase of the recorded data. The overlap 27 may also be enlarged, so that several, for example 5, 4, 3, or 2 magnetic resonance data sets may be acquired for a table position in the internal region of the k-space. This may be achieved by lowering the velocity of the table movement, for example.

The speed of the moving table is preferably in conformity with the speed at which the contrast agent is distributed through the circulatory system, so that the contrast agent bolus may be followed. At a predetermined table position, whereby, for example, the feet of the person being examined are located in the examination region, the table is stopped in step 207.

While the table is at rest, a recording of further magnetic resonance data takes place in step 208, whereby the recordings for predetermined k-space points alternates between a first k-space region and a second k-space region.

A sampling sequence is used to record magnetic resonance data for the predetermined points to be sampled in the k-space, which will be described in detail with regard to the FIGS. 4, 5, and 6 in the following. Specifically, first, an initial inner region of k-space, and subsequently an outer region of k-space will be sampled. The density of the points to be sampled in the outer region is lower than that in the inner region, and as such, the recording process is accelerated, and several recorded data sets for the outer region may be used for reconstruction of a single time step based on a data set of the inner region. This view sharing process allows for an accelerated recording of the magnetic resonance data, while simultaneously improving the image quality. The recording of the magnetic resonance data includes, of course, additional steps, such as the application of a view selection gradient and the irradiation by an RF pulse to stimulate the selected view. These steps are familiar to those of ordinary skill, and therefore need not be further described herein. With the present design version, the recording process is applied to a table at rest. With other design versions of the invention, the recording process may also be applied, however, to a moving table.

With an immobile table in particular, a number of magnetic resonance data sets are recorded, which represent an early, middle and late phase of the contrast agent distribution in an object to be examined. These are, for example, an arterial, a venal and a late contrast agent phase. In this manner, with an immobile table, a time series of image data from the distal region of the field of view may be recorded. The time steps of the time series are indicated by the reference numbers 28, 29, and 30 in FIG. 3. It should be clear that these magnetic resonance data sets represent that part of the person being examined which is located in the examination region which may be shown in a three dimensional form.

Because MR data from the distal region of the viewing field are acquired while the table is at rest, there is no conflict between the described view sharing process and a correction for non-linearity in the magnetic field gradients. This correction may be carried out, for example, on the magnetic resonance data which is recorded during the movement of the table, whereby from said, in particular with a slight overlapping, image data that is not time-resolved is reconstructed. As these data must be non-time-resolved, the application of a view sharing process is not necessary here. This may be used, however, with acquisitions of magnetic resonance data taken on an immobile table. With a process of this sort, the line length 26 may be 30-40 cm with an overlap 27 of 5 cm.

It should however be clear that with other design versions, a view sharing process may be used also during the movement of the table.

In a subsequent step 209, a reconstruction of a static image data set for the entire viewing field as well as a time-resolved image data set for the distal viewing field may be carried out using the time series of the magnetic resonance data sets 28, 29, and 30. Each image data set of the distal viewing field can be combined with the other, entire viewing field in order to obtain a time series of images for the entire viewing field. This time series is static at the proximal ends, i.e. not time-resolved, and is time-resolved at the distal ends. Alternatively the image data sets of the distal viewing field may also be stored in addition to an image data set of the entire viewing field which corresponds to a specific recording period.

As mentioned, the time series of image data allows for observing the distribution of the contrast agent in, for example, the feet of the subject. Furthermore, with subjects having a peripheral arterial obstruction disease, for which the contrast agent arrives at different times in the feet of the subject, a reliable separation of arteries and veins may be obtained with the time series of image data. This is particularly possible through the use of a view sharing process, in which the temporal resolution of the time series may be increased.

The recording sequence, which may be used with a moving table as well as an immobile table, will be described in the following based on FIGS. 4-6.

Figure 4:
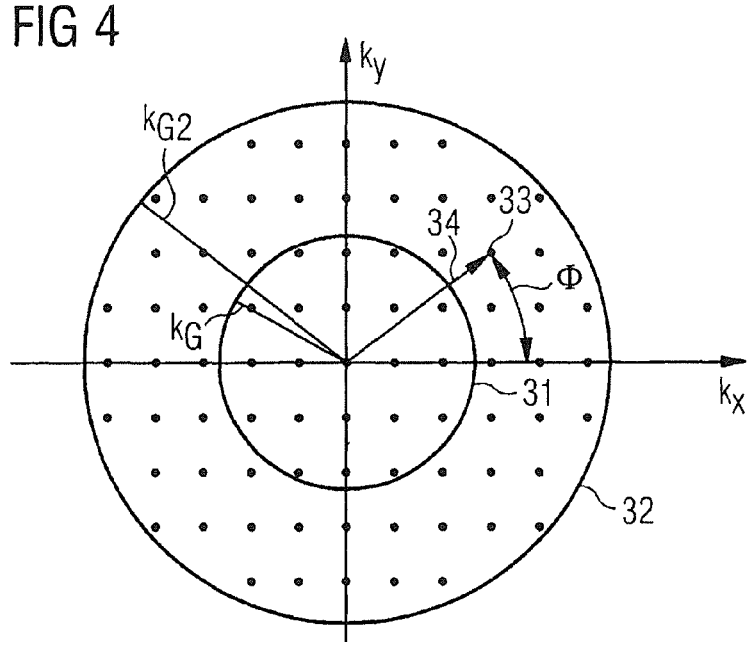
FIG. 4 schematically illustrates predetermined points to be sampled in k-space which are located in a first region and a second region.

FIG. 4 shows predetermined points in k-space having the axes $k_x$ and $k_y$. As mentioned, a frequency coding takes place on the z axis, where thereby each point corresponds to a data line in the z axis. K-space is divided into a first, inner region 31, and a second, outer region 32. The separation is made based on a limit radius $k_g$, i.e. points with a radial distance to the center of k-space having a value smaller than $k_g$ lie within the first region 31. Points with having a larger radial distance, which is however less than $k_{g2}$, lie within the second, or outer region 32. Black points in FIG. 4 represent predetermined points on which k-space is to be sampled. The position of a predetermined point, such as point 33, for example, may be described by the radial distance 34 of the point to the center of k-space and the azimuth angle $\Phi$.

With the present design version, the sampling of k-space is carried out by alternately recording the magnetic resonance data for the first region 31 and the second region 32. The acquisition sequence for sampling the first region 31 employs a trajectory, which is initially an expanding spiral, and subsequently a contracting spiral, so the trajectory contains each of the predetermined points in region 31. Region 32 is also sampled with a trajectory following a spiral that first expands, and subsequently contracts, whereby this trajectory only contains, for example, every second point in a sampling sequence. With a subsequent sampling step of the second region 32, a trajectory of the same shape is used that contains the rest of the points, in order that, for example, after two sampling steps, magnetic resonance data for all of the predetermined points of the second region will be acquired. Other trajectories may also be used, which, for example, contain only every fourth point of the second region 32, in order that this region may be more rapidly sampled. Consequently, the density of the points which are to be sampled in a sampling sequence is higher in the first region 31 than in the second region 32. This is advantageous, as the magnetic resonance data of the inner region is largely responsible for the contrast in the reconstructed image data.

Figure 5:
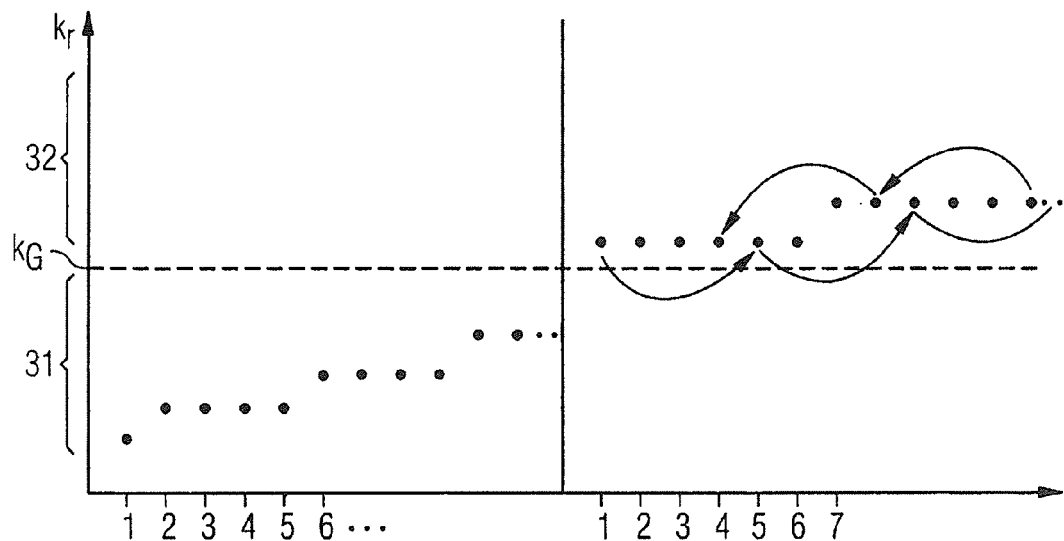
FIG. 5 schematically illustrates the sampling of the predetermined points in a first region and a second region of the k-space.

In order to generate the trajectory for a recording sequence of a region, the predetermined points are arranged as is shown in FIG. 5. The arrangement is made primarily according to the radial distance of the points from the center of k-space, with points with identical radial distances being defined according to the azimuth angle $\Phi$. The phase coding is obtained in that first, magnetic resonance data for the first region is recorded for every second point, for example the odd numbered points. This corresponds to an expanding spiral shaped trajectory in the first region. Subsequently, starting from the outer edge, magnetic resonance data is recorded for the rest of the points in region 31, e.g. the even numbered points. This corresponds to a contracting spiral trajectory. After completion of this sampling sequence, magnetic resonance data will have been recorded for each of the predetermined points in the first region 31.

The acquisition (data entry) sequence for the second region 32 corresponds to the sequence for the region 31, but here the first trajectory contains only every fourth point, for example. This is indicated with an arrow in FIG. 6. The second, contracting trajectory contains another portion of the points in the second region, which is also indicated by arrows. After recording magnetic resonance data along both trajectories, in the present example only half of the points in the second region have been sampled. The rest of the points will be sampled with similar trajectories in a subsequent sampling step of the second region.

Figure 6:
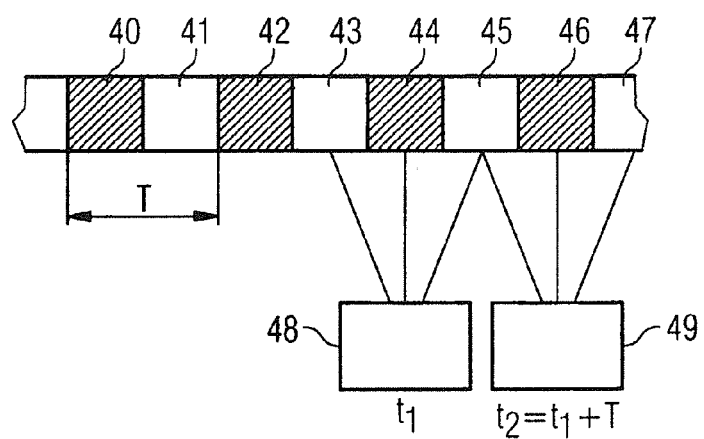
FIG. 6 schematically shows the temporal sequence of a sampling of a first and a second k-space region, as well as the utilization of the acquired magnetic resonance data of the various regions for reconstructing image data corresponding to various time steps.

A sequence for acquiring the magnetic resonance data from the first and second regions is schematically shown in FIG. 6. All of the predetermined points lying in the first region 31 are sampled in the periods 40, 42, 44, and 46, i.e. magnetic resonance data for these points is recorded. In periods 41, 43, 45, and 47, only half of the predetermined points lying in the second region 32 are sampled. A time-resolution T may be obtained using magnetic resonance data recorded in this manner. To reconstruct an image data set 48, a view sharing process is used, whereby magnetic resonance data from the second region 32 recorded in both the period 43 as well as period 45 is used. In this manner, a complete magnetic resonance data set is available for the reconstruction of image data from the second region as well, which however corresponds to two different time periods. Furthermore, a magnetic resonance data set recorded during the period 44 is used for the first region 31. The same applies for the reconstruction of the image data set 49, with magnetic resonance data from the periods 45 and 47 being used for the second region 32. Magnetic resonance data acquired during the period 45 is used for reconstruction of the image data set 48 as well as the image data set 49. Because only half of the predetermined points of the second region are sampled in the periods 41, 43, 45, and 47, the time required is reduced by a factor of 2, which leads to a significant improvement of the recording speed and time-resolution.

In summary, the present invention allows for time-resolved acquisition of magnetic resonance data with both a moving table and an immobile table. Ideally, a static image data set is reconstructed with a moving table, whereas with an immobile table the reconstruction of a time-resolved image data set is obtained, which allows for the observation of the contrast agent distribution in the circulatory system in the distal region of the subject. The process makes this possible in that a computing time-optimized correction of non-linearities in the magnetic field gradients may be carried out with a moving table and at the same time time-resolved data regarding the distribution of the contrast agent may be obtained. In particular, the process allows for the execution of a contrast agent enhanced MR-angiography with a large viewing field using a magnet of a shorter dimension in the longitudinal direction. The entire process may be carried out fully automatically, which also provides for an improvement in the workflow. By recording the entire viewing field during a scanning with a moving table, the necessary scanning time may furthermore be reduced, which consequently leads to a better use of the magnetic resonance imaging scanner and a reduction in costs.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring time-resolved magnetic resonance data from an examination region of a magnetic resonance data acquisition unit comprising the steps of:
   acquiring magnetic resonance signals from the examination region while an examination subject is moved continuously through the examination region on a continuously moving table and, prior to acquiring said magnetic resonance signals, implementing a phase coding in order to designate respective positions in k-space at which respective positions, respective data entries will be made in k-space representing said magnetic resonance signals;
   interrupting movement of said table at a predetermined table position;
   continuing the acquisition of magnetic resonance signals from the examination region during a predetermined time period while said table is at rest in said predetermined position;
   implementing said phase coding along two axes of k-space with said table at rest by acquiring, in alternation, a predetermined number of magnetic resonance signals that fill a first region of k-space with said data said first region containing points in k-space having a radial distance to a center of k-space that is less than a predetermined limit value, and a predetermined number of magnetic resonance signals that fill a second region of k-space with said data, said second region as containing points in k-space having a radial distance to the center of k-space that exceeds said predetermined limit value; and
   in a computer, reconstructing an image using a time series comprising time series segments comprising said data acquired from said first region of k-space this alternate with time series segments comprising said data acquired from said second region of k-space.

2. A method as claimed in claim 1 comprising implementing said phase coding by sampling said first region of k-space with a single spiral trajectory and sampling said second region of k-space with at least two spiral trajectories.

3. A method as claimed in claim 1 comprising sampling k-space at predetermined points within said first region and said second region, and arranging said predetermined points to establish a sampling trajectory with respect to a radial distance of the predetermined points to a center of k space and an azimuth angle relative to a position in k-space of said predetermined points.

4. A method as claimed in claim 3 comprising sampling said first region using at least one sampling sequence wherein the radial distance of said predetermined points increases, and a sampling sequence wherein the radial distance of the predetermined points decreases, each of said sampling sequences comprising different points among said predetermined points.

5. A method as claimed in claim 4 comprising sampling said second region of k-space using a sampling sequence wherein the radial distance of the predetermined points increases and a sampling sequence wherein the radial distance of the predetermined points decreases, each of said sampling sequences for sampling said second region containing different points among said predetermined points, and when sampling said second region, sampling one-half or less of said predetermined points.

6. A method as claimed in claim 1 comprising sampling k-space at predetermined points and, with each sampling of said second region, acquiring magnetic resonance data for only a portion of said predetermined points in said second region and sampling magnetic resonance data for a remainder of said predetermined points in at least one of a prior sampling of said second region and a subsequent sampling of said second region.

7. A method as claimed in claim 6 comprising reconstructing an image from the sampled predetermined points in k-space in said first region and in said image reconstruction, using additional magnetic resonance data acquired in at least one prior sampling of said second region and at least one subsequent sampling of said second region.

8. A method as claimed in claim 1 comprising implementing phase coding with said table moving by sampling k-space at predetermined points in a grid array.

9. A method as claimed in claim 1 comprising implementing said phase coding along two axes of k-space, and additionally implementing frequency coding in a third axis of k-space substantially parallel to a movement direction of said table, and implementing a partial image reconstruction of said magnetic resonance data acquired while said table is moving by transforming data in k-space along the direction of said frequency coding.

10. A method as claimed in claim 1 wherein said examination subject is a living subject having a circulatory system, and comprising introducing a contrast agent bolus into said circulatory system and coordinating a speed of movement of said table with a speed of movement of said contrast agent bolus in said circulatory system.

11. A method as claimed in claim 1 wherein said examination region has a predetermined length in a direction parallel to the direction of movement of said table, and moving said table at a speed between repeated sampling of the same predetermined points in k-space by at least half of said predetermined length.

12. A method as claimed in claim 1 comprising implementing said phase coding by activating magnetic field gradients exhibiting a non-linearity, and automatically electronically correcting for said non-linearity of said magnetic field gradients.

13. A method as claimed in claim 12 comprising sampling k-space in a grid array, and automatically correcting said non-linearity of said magnetic resonance field gradient by correcting said grid array.

14. A method as claimed in claim 1 wherein said examination subject is a human being, and comprising setting said predetermined table position to coincide with location of a foot end of said human being in said examination region.

15. A method as claimed in claim 1 comprising reconstructing a static image of the examination subject from a static image data set acquired while said table is moving, and reconstructing a time-resolved image of the examination subject from magnetic resonance data acquired while said table is at rest.

16. A method as claimed in claim 15 comprising acquiring said static image data set from a region of the examination subject that is moved through the examination region and combining said static image data set with an image data set acquired while said table is at rest with a food end of the examination subject in said examination region, and reconstructing a time series of images from said combined dataset.

17. A method as claimed in claim 16 wherein said examination subject has a circulatory system and comprising introducing a contrast agent bolus into the circulatory system, and acquiring said static image data set to contain at least three phases of said contrast agent bolus distributed in said circulatory system.

18. A method as claimed in claim 17 comprising additionally acquiring magnetic resonance signals from the examination subject with said table at rest before acquiring magnetic resonance signals from the examination subject with the table moving.

19. A magnetic resonance imaging apparatus configured for acquiring time-resolved magnetic resonance data, comprising:
a magnetic resonance data acquisition unit having an examination region and a patient table movable through said examination region;
a control unit configured to operate said data acquisition unit in order to acquire magnetic resonance signals from the examination region while an examination subject is moved continuously through the examination region on the patient table and, prior to acquiring said magnetic resonance signals, configured to implement a phase coding in order to designate respective positions in k-space at which respective positions, respective data entries will be made in k-space representing said magnetic resonance signals;
said control unit being configured to interrupt movement of said table at a predetermined table position and to continue the acquisition of magnetic resonance signals from the examination region during a predetermined time period while said table is at rest in said predetermined position;
said control unit being configured to implement said phase coding with said table at rest by acquiring, in alternation, a predetermined number of magnetic resonance signals that fill a first region of k-space with said data said first region containing points in k-space having a radial distance to a center of k-space that is less than a predetermined limit value, and a predetermined number of magnetic resonance signals that fill a second region of k-space with said data, said second region as containing points in k-space having a radial distance to the center of k-space that exceeds said predetermined limit value; and
a computer configured to reconstruct an image using a time series comprising time series segments comprising said data acquired from said first region of k-space this alternate with time series segments comprising said data acquired from said second region of k-space.

20. A non-transitory computer-readable data storage medium encoded with programming instructions, said storage medium being loadable into a computer system of a magnetic resonance imaging apparatus having a magnetic resonance data acquisition unit, and said programming instructions causing said computer system to:
operate a magnetic resonance acquisition unit, having an examination region, in order to acquire magnetic resonance signals from the examination region while an examination subject is moved continuously through the examination region on a continuously moving table and, prior to acquiring said magnetic resonance signals, implement a phase coding in order to designate respective positions in k-space, at which respective positions, respective data entries will be made in k-space representing said magnetic resonance signals;
interrupt movement of said table at a predetermined table position;
continuing the acquisition of magnetic resonance signals from the examination region during a predetermined time period while said table is at rest in said predetermined position;
implement said phase coding with said table at rest by acquiring, in alternation, a predetermined number of magnetic resonance signals that fill a first region of k-space with said data said first region containing points in k-space having a radial distance to a center of k-space that is less than a predetermined limit value, and a predetermined number of magnetic resonance signals that fill a second region of k-space with said data, said second region as containing points in k-space having a radial distance to the center of k-space that exceeds said predetermined limit value; and reconstruct an image using a time series comprising time series segments comprising said data acquired from said first region of k-space this alternate with time series segments comprising said data acquired from said second region of k-space.

21. A method as claimed in claim 1 comprising, in said computer, reconstructing said image using data acquired from said first region of k-space in one of said time series segments, and data acquired from said second region of k-space in each of two of said time series segments that are adjacent to said one of said time series segments.

22. An apparatus as claimed in claim 19 wherein said computer is configured to reconstruct said image using data acquired from said first region of k-space in one of said time series segments, and data acquired from said second region of k-space in each of two of said time series segments that are adjacent to said one of said time series segments.

23. A non-transitory computer-readable data storage medium encoded with programming instructions as claimed in claim 20 wherein said programming instructions further cause said computer system to reconstruct said image using data acquired from said first region of k-space in one of said time series segments, and data acquired from said second region of k-space in each of two of said time series segments that are adjacent to said one of said time series segments.

\* \* \* \* \*